US012622440B2

(12) United States Patent
Fridman et al.

(10) Patent No.: US 12,622,440 B2
(45) Date of Patent: May 12, 2026

(54) FOOD AND FRESH PRODUCE DISINFECTION CHAMBER UTILIZING FAST MIXED LIQUID AND NONEQUILIBRIUM PLASMA-GENERATED SPECIES

(71) Applicant: AA Plasma LLC, Philadelphia, PA (US)

(72) Inventors: Gregory Fridman, Philadelphia, PA (US); Randy Richard Cox, Yuma, AZ (US); Charles Christopher Bailey, III, Philadelphia, PA (US)

(73) Assignee: AA Plasma LLC, Grove City, OH (US)

( * ) Notice: Subject to any disclaimer, the term of this patent is extended or adjusted under 35 U.S.C. 154(b) by 816 days.

(21) Appl. No.: 17/999,679

(22) PCT Filed: May 28, 2021

(86) PCT No.: PCT/US2021/070632
§ 371 (c)(1),
(2) Date: Nov. 22, 2022

(87) PCT Pub. No.: WO2021/243371
PCT Pub. Date: Dec. 2, 2021

(65) Prior Publication Data
US 2023/0232870 A1 Jul. 27, 2023

(51) Int. Cl.
*A23B 2/50* (2025.01)
*A23B 2/721* (2025.01)
(Continued)

(52) U.S. Cl.
CPC ............... *A23B 2/50* (2025.01); *A23B 2/721* (2025.01); *B01F 23/23121* (2022.01); *B01F 23/705* (2022.01); *A61L 2202/122* (2013.01)

(58) Field of Classification Search
CPC .. B01F 25/21; B01F 25/312; B01F 25/31242; B01F 25/4314; B01F 25/52; B01F 25/64;
(Continued)

(56) References Cited

U.S. PATENT DOCUMENTS 4,750,917 A * 6/1988 Fujii ....................... B03C 3/383
422/24
5,993,738 A * 11/1999 Goswani ................... B03C 3/60
422/4
(Continued)

FOREIGN PATENT DOCUMENTS

EP        2411058 A1    2/2012
JP     2014-030425 A    2/2014
WO  WO/2010/030039 A1   3/2010

OTHER PUBLICATIONS

International Search Report issued in International Application No. PCT/US2021/070632 dated Sep. 14, 2021.

*Primary Examiner* — Hung D Nguyen
(74) *Attorney, Agent, or Firm* — Vos-IP, LLC

(57) ABSTRACT

A device for creating reactive oxygen and reactive nitrogen species comprising: a plasma generator comprising at least one electrode positioned within an open-ended chamber and a centrifugal mixing chamber in fluid communication with the plasma generator, said centrifugal mixing chamber comprising a mixing chamber side wall and a blade, said blade oriented to allow passage of air in a circular motion around a central post of said centrifugal mixing chamber, and an exit nozzle on an opposing end of said centrifugal mixing chamber.

14 Claims, 13 Drawing Sheets

(51) Int. Cl.
    *B01F 23/231*      (2022.01)
    *B01F 23/70*       (2022.01)

(58) Field of Classification Search
    CPC .............. B01F 33/821; B01F 23/21321; B01F
                      23/23342; B01F 23/454; B01F 23/53;
               B01F 23/59; B01F 23/705; A61L 2/00;
               A61L 2/14; A61L 2/18; A61L 2/186;
             A61L 2/208; A61L 2/22; A61L 2/24;
                 A61L 2/26; A61L 2202/11; A61L
         2202/122; A61L 2202/13; A61L 2202/14;
          A61L 2202/15; A61L 2202/21; A23B
             2/50; A23B 2/60; A23B 2/704; A23B
         2/708; A23B 2/721; A23B 2/725; A23B
                2/792; A23L 3/26; A23L 3/3445
    See application file for complete search history.

(56)               References Cited

U.S. PATENT DOCUMENTS

| | | | |
|---|---|---|---|
| 8,372,183 B2 * | 2/2013 | Doucette ................... | B03C 3/70 |
| | | | 96/26 |
| 2012/0093691 A1 * | 4/2012 | Mole ......................... | F24F 8/80 |
| | | | 422/310 |
| 2013/0272929 A1 * | 10/2013 | Pelfrey .................... | A61L 2/22 |
| | | | 422/186.04 |

* cited by examiner

Spraying Plasma Pretreated
Water for 5 Seconds

Droplet Explosion in Plasma

Droplet Explosion in Plasma (cont'd)

FOOD AND FRESH PRODUCE DISINFECTION CHAMBER UTILIZING FAST MIXED LIQUID AND NONEQUILIBRIUM PLASMA-GENERATED SPECIES

CROSS-REFERENCE TO RELATED APPLICATIONS

This application is a 371 National Phase Entry of International Patent Application No. PCT/US2021/070632 filed on May 28, 2021, which claims the benefit of U.S. Provisional Patent Application No. 62/704,820 filed on May 29, 2020, with the United States Patent and Trademark Office, the contents of which are incorporated herein by reference in their entirety.

FIELD OF THE INVENTION

The present invention is related to devices for sanitization, disinfection, and/or sterilization of fresh produce, meat, poultry, fish, and other perishable materials utilizing plasma generated radicals in fluid, as well as methods of use of the same with devices and in enclosed environments such as refrigeration containers.

BACKGROUND OF THE INVENTION

As soon as produce is harvested, there is a rush to cool the produce to maintain freshness. Chilling the produce to just above freezing dramatically increases the shelf life of the produce after harvest, as compared to produce that is not chilled. This is most apparent for vegetables as compared to whole fruits, as whole fruits typically have shells intended to protect the fruit (imagine an apple) once it is separated from the parent plant, whereas vegetables are literally a portion of the parent plant (i.e., lettuce).

The same issue is found with meats including red and white meats as well as poultry, and also with fish. Red meat produce is slaughtered and then exsanguinated before being butchered into particular cuts of meat. This process is similar for pork, lamb, and other non-beef meats. Poultry also utilizes a similar process, though there are additional processing steps for feather removal.

In each case, these types of meat are frequently ground, cut, or otherwise handled with or without skin and these various handling steps provide opportunity for introduction of vegetative bacteria, viruses, bacterial or fungal spores, and the like, which can spoil the food. Topical materials like sodium hypochlorite are frequently added to meats to inactivate pathogenic organisms on the meat for storage and human consumption, in order to increase the safety of consuming these meats in their refrigerated or frozen states.

Fish, both freshwater and saltwater varieties, face similar hurdles in processing. In longline fishing, most fish are flash frozen once they are caught in order to maximize the meat quality and freshness to 0° F. or even to −20° F. or lower. For farmed fish, the process may or may not include this flash freezing step, and instead may simply gut and sell the materials as fresh. In either case, there remains a goal to reduce or eliminate the introduction of bacteria or viruses to the fish to ensure that it is safe for later human consumption. Accordingly, like meat, certain preservatives and sterilizing compounds are added to prevent attack by viral, bacterial, and fungus.

New devices and processing strategies are needed, which are more efficient and use fewer chemicals than present strategies. Applicant has created a novel device and method of treating whole and cut produce, meats, poultry, fish, and other perishable items utilizing plasma dissolved within microdroplets of fluid.

SUMMARY OF THE INVENTION

The present disclosure details a new device for generating reactive oxygen and nitrogen species using cold plasma, which are combined with microdroplets of fluid, wherein the reactive oxygen and nitrogen species are dissolved into the microdroplets, which conserves and protects these highly unstable and reactive species and wherein the microdroplets are then expressed into a container or onto the materials to coat perishable items such as produce to sanitize, disinfect, and/or sterilize the perishable items. Advantageously, in certain embodiments, the devices detailed herein can utilize vacuum containers wherein when the vacuum is terminated, the rush of air through a valve is utilized to move the reactive species, generated in plasma, and to circulate charged microdroplets into the vacuum container.

In a preferred embodiment, a device for creating charged microdroplets comprising: a centrifugal mixing chamber for receiving atomized microdroplets, a plasma generator comprising at least one electrode positioned within an open-ended chamber; wherein said centrifugal mixing chamber comprises a blade to orient a flow of air and microdroplets from one end of the centrifugal mixing chamber to a second end.

In a further preferred embodiment, the device wherein the plasma generator is positioned before the centrifugal mixing chamber.

In a further preferred embodiment, the device wherein the plasma generator is positioned after the centrifugal mixing chamber. In a further preferred embodiment, the device wherein said open-ended chamber having a first end (16) and a second end (17), with the first end and the second end open to allow passage of air through the open-ended chamber; an air filter positioned at the first end; and an atomizing cavity (41) having a first cavity end in fluid contact with the second end, a second cavity end, and a side wall, said side wall comprising at least one aperture (4a) thereto, and at least one nozzle (81) affixed into said aperture; wherein the centrifugal mixing chamber (5) is contiguous with the second cavity end, said centrifugal mixing chamber comprising a mixing chamber side wall and the blade (14), said blade oriented to allow a passage of air in a circular motion around a central post (31) of said centrifugal mixing chamber, and an at least one exit nozzle (6) on an opposing end of said centrifugal mixing chamber.

In a further preferred embodiment, the device wherein said open-ended chamber having a top, a bottom, two sides, and said at least one electrode positioned within said open-ended chamber.

In a further preferred embodiment, the device further comprising a fan. In a further preferred embodiment, the device wherein the fan pulls air through an air filter.

In a further preferred embodiment, the device further comprising a pump and a fluid vessel, said pump attached to said fluid vessel and pumping fluid through an at least one nozzle.

In a further preferred embodiment, the device wherein said plasma generator comprises at least two electrodes stacked on top of one another, wherein the two electrodes are positioned to allow the flow of air above and below each of the two electrodes within the open-ended chamber. In a further preferred embodiment, the device wherein said pump generates nebulized fluid.

In a further preferred embodiment, the device wherein the pump is disposed of below the centrifugal mixing chamber. In a further preferred embodiment, the device wherein the pump is placed between 0.01 meter and 3 meters below the centrifugal mixing chamber.

In a further preferred embodiment, the device comprising an atomizing cavity (41) in contact with the centrifugal mixing chamber, said atomizing cavity comprising a first cavity end and a second cavity end, and a side wall, said side wall comprising at least one aperture (4a) thereto, and at least one nozzle (81) affixed into said aperture; wherein the centrifugal mixing chamber (5) is contiguous with the second cavity end, said centrifugal mixing chamber comprising a mixing chamber side wall and the blade (14), said blade oriented to allow passage of air in a circular motion around a central post (31) of said centrifugal mixing chamber, and an at least one exit nozzle (6) on an opposing end of said centrifugal mixing chamber, which is in contact with the plasma generator.

In a further preferred embodiment, the device further comprising a drain. In a further preferred embodiment, the device wherein the drain connects to either the fluid vessel or is disposed.

In a further embodiment, a method to reduce bacterial or viral loads on produce within a pressurized chamber comprising: creating a vacuum within said pressurized chamber; opening a valve in the pressurized chamber, said valve operably connected to a plasma generating device to generate reactive oxygen and nitrogen species; expressing microdroplets into a centrifugal mixing chamber; mixing the microdroplets with said reactive oxygen and nitrogen species to form charged microdroplets; expelling the microdroplets, the reactive oxygen and nitrogen species, and the charged microdroplets into the pressurized chamber; and sealing the pressurized chamber after a predetermined amount of time, wherein the charged microdroplets contact at least one perishable item within the pressurized chamber.

In a further preferred embodiment, the method wherein the microdroplets and the reactive oxygen and nitrogen species are rotated within the centrifugal mixing chamber; wherein the centrifugal mixing chamber forces a portion of microdroplets to condense on a wall of the centrifugal mixing chamber.

In a further preferred embodiment, the method wherein said plasma generating device comprising at least one electrode positioned within an open-ended chamber, said open-ended chamber having a first and second end, with the first and second ends open to allow passage of air through the open-ended chamber.

In a further preferred embodiment, the method further comprising an air filter positioned at the first end.

In a further preferred embodiment, the method further comprising an aperture for expressing microdroplets into the centrifugal mixing chamber and comprising at least one nozzle affixed into said aperture for expressing the microdroplets.

In a further preferred embodiment, the method wherein the step of mixing the microdroplets with the reactive oxygen and nitrogen species is performed by mixing within a centrifugal mixing chamber.

In a further preferred embodiment, the method wherein said centrifugal mixing chamber comprises a central post and an exit nozzle on an opposing end.

In a further preferred embodiment, the method wherein the plasma generating device comprises a plurality of electrodes, and wherein said plurality of electrodes generate plasma for at least one minute, which is sufficient to generate between 0.1 ppm and 1,000 ppm of plasma.

In a further preferred embodiment, the method further comprising the step of activating a fan within said pressurized chamber to circulate the charged microdroplets within the pressurized chamber.

In a further preferred embodiment, the method wherein the pressurized chamber is a 57 $m^3$ vacuum chilling container.

In a further preferred embodiment, the method wherein the valve in the pressurized chamber generates a flow of between 500 cfm and 1500 cfm when releasing the vacuum.

In a further preferred embodiment, the method wherein the predetermined amount of time is at least thirty seconds. In a further preferred embodiment, wherein the predetermined amount of time is between 30 seconds and 24 hours.

In a further embodiment, a centrifugal mixing chamber for generating charged microdroplets, said centrifugal mixing chamber comprising a first end and a second end, a central post, and a blade structure rotating around said central post; a plasma generating element connected to either the first or said second end; wherein a flow of air is generated from the first end to the second end wherein reactive oxygen and nitrogen species generated from the plasma generating element are introduced to microdroplets; wherein the blade structure forces a portion of microdroplets to condense on a wall of the centrifugal mixing chamber, thereby reducing average size of the microdroplets being expelled from the centrifugal mixing chamber.

In a further embodiment, a high flow mixing chamber for generating charged microdroplets comprising: a centrifugal mixing chamber, a plasma generating element, a fan, and a pump; said fan positioned to force air through the centrifugal mixing chamber; said pump engaged to a nozzle for expressing fluids into said centrifugal mixing chamber; and said plasma generating element placed in line with said centrifugal mixing chamber to receive microdroplets from a nozzle on said centrifugal mixing chamber.

In a further embodiment, a container for sterilizing perishable items comprising: a container, a fan, a centrifugal mixing chamber, a plasma generating element, and a pump; said fan positioned to force air through the centrifugal mixing chamber; said pump engaged to a nozzle for expressing fluids into said centrifugal mixing chamber; and said plasma generating element placed in line with said centrifugal mixing chamber; wherein microdroplets are introduced to RONS generated from said plasma generator, thereby charging said microdroplets; and releasing said microdroplets into said container.

Figure 1A:
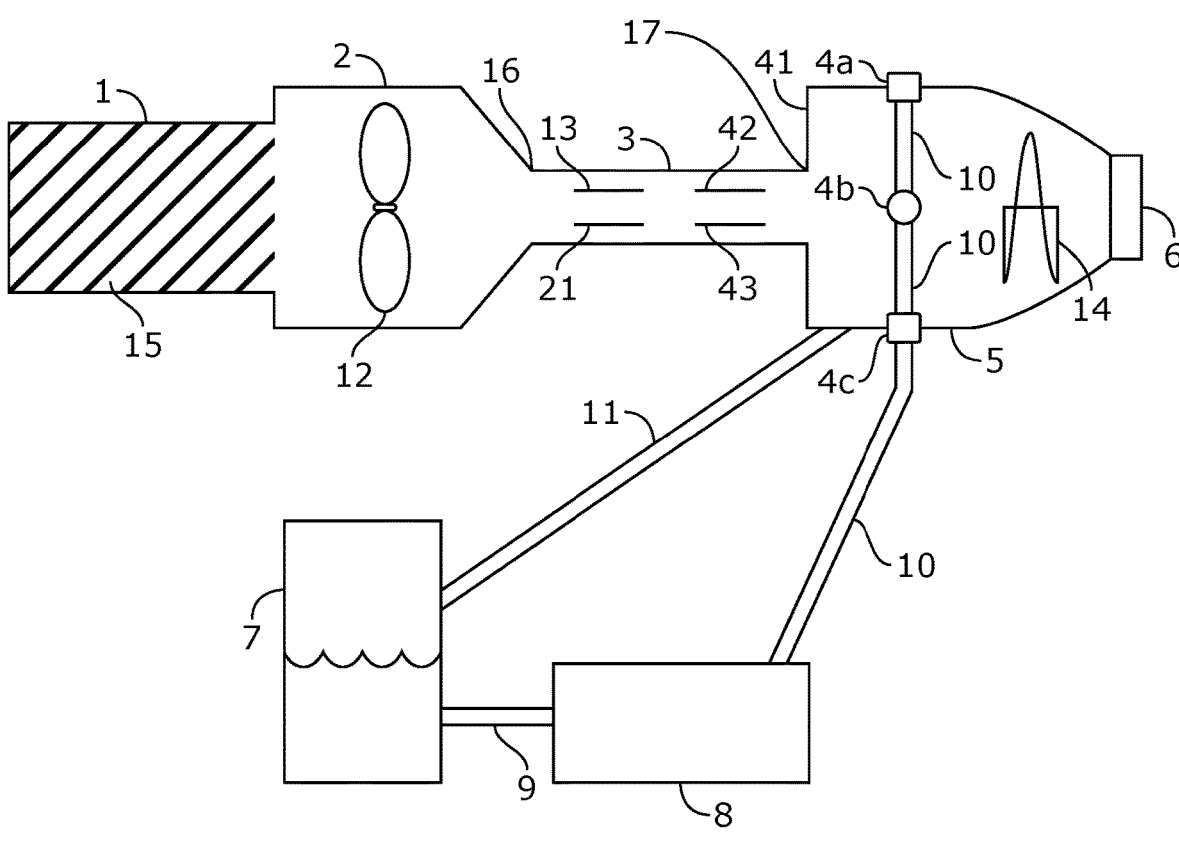
FIGS. 1A and 1B detail variations of embodiments of the present disclosure of a device for generating microdroplets saturated with plasma generated radicals.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The device and methods described herein are particularly suited for generating reactive species which are dissolved into fluid droplets to conserve and protect the reactive species. This is particularly relevant to sanitization, disinfection, and sterilization processes, specifically for perishable items. The terms sanitize, disinfect, and sterilize mean generally to reduce the quantities of the pathogens by x-log as required for the particular perishable item. Notably, different perishable items have different requirements for reduction of pathogens in order to meet these definitions. Those of ordinary skill in the art will recognize that these values can be determined by reviewing the definitions for the particular item of interest.

As used herein, a "perishable item" means produce, or meats that are whole or cut, or another item that needs to be disinfected.

As used herein "meats" means red meat including but not limited to beef, buffalo, and similar meat, white meat including but not limited to pork, goat, venison, poultry, and fish.

As used herein "produce" means whole or cut fruits, vegetables, tubers, and other edible food materials which are grown whether on a tree, bush, shrub, a plant itself, or in the ground.

As used herein the term "pathogens" shall mean bacterial spores, mycobacteria, viruses, nonlipid or small viruses, fungi, vegetative bacteria, fungal spores, and lipid or medium size viruses.

Disinfection devices disclosed herein include a cold plasma generator. The term "cold plasma" as used herein refers to a plasma which is not in thermodynamic equilibrium, particularly that the temperature of the electrons is much higher than the temperature of ions and neutrals. The term "cold plasma" as used herein is synonymous with the terms "nonthermal plasma" and "nonequilibrium plasma." The cold plasma generators of the disinfection devices disclosed herein may include any generator known to generate a cold plasma. Examples of cold plasma generators which may be used for the disinfection devices disclosed herein include but are not limited to glow discharge, corona discharge, atmospheric pressure plasma jet, dielectric barrier discharge, micro-hollow cathode discharge, plasma needle and low-pressure plasma. Furthermore, the cold plasma generators considered for the disinfection devices disclosed therein may include pulsed cold plasma generators or continuous wave cold plasma generators.

Both pulsed and continuous-wave dielectric barrier discharge cold plasma generators were used in the development of the disinfection devices disclosed herein and are known to function particularly well with the design considerations discussed herein. Advantages of dielectric barrier discharge cold plasma generators is small size, making them easily configured, and deployed into an enclosure. Continuous wave dielectric barrier discharge cold plasma generators are advantageous due to their availability and lower costs as compared to pulsed dielectric barrier discharge cold plasma generators. Yet, a disadvantage of employing continuous wave dielectric barrier discharge cold plasma generators is that they generate considerably more ozone in a given disinfection process as compared to pulsed dielectric barrier discharge cold plasma generators.

Each of the disinfection devices disclosed herein also preferably incorporates an atomizer nozzle to generate microdroplets of less than 10 microns in average size. One such example of an atomizer nozzle incorporates a nebulizer. While any type of nebulizer may be used in the disinfection devices disclosed herein, it preferable to utilize a nebulizer or atomizer that is configured to generate droplets having an average diameter of 10 microns or 5 microns or smaller. (The size of the microdroplets follows a bell curve on the size distribution, and thus there is variance in the size of the microdroplets.) In particular, small droplets not only allow for saturation of perishable items, but also increases the rate of transmission of the RONS species into the droplets because of the high surface area of the droplets. Thus, the smaller particle sizes are significantly more effective at reducing pathogen loads as compared to larger fluid droplets.

Fresh produce is grown both in the ground and in greenhouse settings. Both settings, however, allow for the germination of and contact with pathogens, which, left unchecked, can rapidly multiply. When produce is cut from the field, for example, asparagus, the tips are cut off of the plant and begin to degrade immediately. In a home garden, an individual would cut the asparagus and then bring it inside to cook the freshly cut asparagus. Alternatively, an individual might refrigerate the cut asparagus or place them in fluid at the cut end. All of these actions either use the material after it is freshly cut or preserve the cut asparagus to maintain its freshness. In commercial growing, there might be thousands of pounds of asparagus cut from a hot field and which are not able to be cooked or individually treated as in a home garden. The volume of material and the temperature means that the asparagus may not be quickly processed and thus increases the risk of spoilage. Accordingly, to better preserve the asparagus, quickly chilling the cut asparagus leads to improved freshness and preservation.

Simultaneously, however, vegetables may be damaged in transport, or simply because of their growth on fields, may carry pathogens. Therefore, it is important that the vegetables are cleaned to prevent the growth and proliferation of pathogens and that these pathogens are not transported on the produce to cross-contaminate other materials. This is where there is value in sanitization, disinfection, and sterilization procedures.

This same issue occurs with meats. Typical processing includes slaughter and exsanguination followed by chilling. The meat is then butchered, which introduces numerous contact points with the meat and thus the possibility of the introduction of pathogens. Accordingly, the meat must be properly cared for to prevent the transmission and/or growth of pathogens. For example, salmonella is a common bacterium that proliferates on meat, yet can be controlled with effective sanitization, disinfection, and/or sterilization procedures. Typically, chlorine gas or peracetic acid, as two examples, are used for these processes and which inactivate or destroy pathogens form the surface of the meat.

Historically, perishable items such as cut produce are washed with large quantities of water, such as 500 gallons or 1,000 gallons or more for a given load, which functions to both cool the produce, but also removes dirt and some surface pathogens. This, wash, however, is wasteful and does not specifically deal with the disinfection of pathogens which remain on the surface in potentially large quantities and which water alone is not sufficient to remove. This process also promotes cross-contamination of foods and produces by moving pathogens around without actually disinfecting or destroying those pathogens.

Spoiling materials also provide ripe grounds for promoting additional pathogenic growth. Chilling of perishable items is critically important to preserving freshness and preventing and reducing spoilage. Chilled transport vehicles are frequently utilized to quickly chill produce that is placed within the vehicle's container. For example, vacuum chilled containers are commonly utilized, having a size of approximately 57 m$^3$ and can hold and chill significant amounts of produce. Simultaneously, this vessel can be fitted to allow for washing and cleansing by spraying of charged microdroplets to sanitize, disinfect, and/or sterilize the items.

Applicant has generated a new device that utilizes plasma generation, in conjunction with fluid droplets, which allows for dramatic kill rates of pathogens on the surface of perishable items. FIG. 1A details an overview of an embodiment of a sterilization device of the present disclosure. Beginning on the left, an air filter (1) is provided with a replaceable filter media (15). The air filter (1) is positioned adjacent to a fan (2), having a fan blade (12). Together, the air filter (1) and the fan (2) work to pull air through the air filter and provide clean air at an appropriate rate to the plasma generator (3). The plasma generator (3) comprises at least one electrode, but preferably comprises upper electrodes (13) and lower (21) electrodes, which are stacked upon one another. As depicted in FIG. 1A, there is a second set of electrodes in line with the first set, namely the rear upper electrode (42) and rear lower electrode (43). The plasma generator (3) creates nonthermal plasma as the air is passed over the upper (13) and lower electrodes (21) (and the rear upper and lower electrodes [42 and 43]). This creates reactive nitrogen and oxygen species (RONS). The now charged air passes into the fluid atomizer cavity (41). The atomizer comprises at least one intake port but is depicted here with three intake ports (4a, 4b, and 4c), which are openings in the atomizer cavity (41), with each opening containing an atomizer nozzle. The atomizer nozzles (81 in FIG. 4) are connected via tubing (10) to a pump (8), which is connected to a fluid reservoir (7). The pump (8) and fluid reservoir (7) are connected with a tubing (9) to draw fluid from the fluid reservoir (7) to the pump (8), and pump forces the fluid through the atomizer nozzles, which can be connected via the tubing (10) in series or individually.

Species such as ozone (O$_3$), hydroxyl radical (OH), hydrogen peroxide (H$_2$O$_2$), singlet oxygen (O$_2$*), peroxynitrite radical (ONOO*), and others are generated by the plasma generator (3) and these species are conserved and protected by being dissolved into the fluid microdroplets. A drain line (11) is attached to the fluid atomizer cavity, which captures fluids that collected at the bottom of the atomizer cavity to return the fluids back to the reservoir (7) or to a drain as appropriate. The fluids coming from the drain line (11), are charged with the reactive species (RONS), and the fluid retains the dissolved RONS. This allows fluid that is nebulized or atomized to already have some charges and to be more easily saturated with reactive species, when such is used with a recirculating system. Alternatively, the fluid can be drained to a further storage tank, where the charged fluid can be used for other processing. Finally, the fluid can simply be drained out of the system to waste.

The microdroplets are then forced into the centrifugal mixing chamber (5), which has an auger like blade (14) around a central point, which forces the rotation of the air and microdroplets. This centrifugal mixing chamber (5) forces the charged RONS and microdroplets to rotate in the chamber and this forces more contact between the RONS and the microdroplets, ensuring more RONS are dissolved into the microdroplets, while simultaneously forcing large droplets of fluid to coalesce or condense by the rotation of the microdroplets in this chamber. The coalesced or condensed fluid is drained into the drain line (11). The droplets that are not coalesced or condensed pass around the blade (14) and are expelled through the nozzle ends primarily (6) as charged microdroplets, having been combined with the RONS generated by the plasma generator. These microdroplets can then be utilized to sanitized, disinfect, and/or sterilize perishable items.

In order to sanitize, disinfect, and/or sterilize perishable items, it is necessary to generate sufficient quantities of reactive species (RONS). These reactive species are created by passing air over an electrode and applying high voltage to the electrode. The precise concentration of reactive species and the duration of contact is variable based on the particular product being disinfected, cleaned, or sterilized, and the necessary log reduction required for a particular product.

Figure 1B:
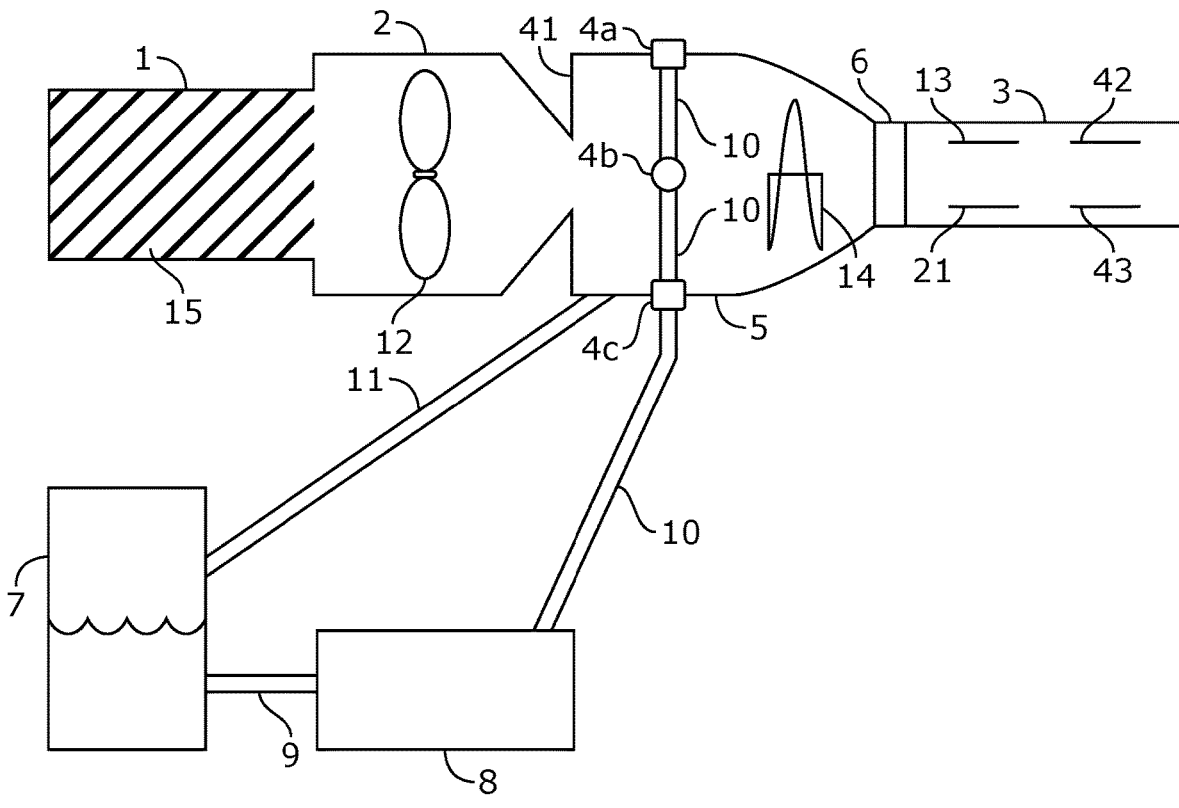

FIG. 1B provides a variation on the embodiment of FIG. 1A, which essentially swaps the position of the centrifugal mixing chamber (5) and the plasma generator (3). Notably, in this embodiment, the microdroplets are created and pass directly through the plasma generator (3) instead of being mixed into the centrifugal chamber (5) with the RONS. Accordingly, it is important to ensure that the size of the microdroplets entering the plasma generator is small enough to not impact and short out the plasma generator (3).

Microdroplets of over ten microns in size are typically those which are impacted by gravity and centrifugal forces and are also large enough to cause a short. Accordingly, there are two elements within the embodiments that assist in reducing the size of the microdroplets. First, the pump (8) and the tubing (10) are positioned below the centrifugal mixing chamber (5) with a distance D of the tubing (10) between the pump and the centrifugal mixing chamber (5). The distance D is typically between 0.01 meter and 3 meters, and most preferably about 0.1 to about 1 meter. The pump forces fluids through an atomizer or nebulizer to create microdroplets. By pumping fluids vertically, the smallest microdroplets will flow through the tube (10), while the larger droplets will be sufficiently impacted by gravity and coalesce and thus will not pass into the centrifugal mixing chamber (5). Once in the centrifugal mixing chamber (5), the act of rotating the microdroplets will again force the largest droplets to coalesce to the sides of the centrifugal mixing chamber (5), removing them from the air, thereby allowing only the smallest particles to pass into the plasma generator (3). The microdroplets then will directly pass through the plasma generator (3) to charge the microdroplets with RONS as they pass through the plasma generator (3). Simultaneously, the microdroplets are exploded as they pass through the plasma generator (3), further reducing their size.

In each of the embodiments for FIGS. 1A and 1B, the device works to generate microdroplets that are saturated with reactive oxygen and nitrogen species. In some of the embodiments, larger microdroplets are returned and circulated, in other embodiments, the larger microdroplets are disposed. Passing microdroplets through the plasma generator generates microdroplet explosion, further reducing the size of the microdroplets, thus increasing efficiency because the smaller droplets generate greater surface areas.

Figure 2:
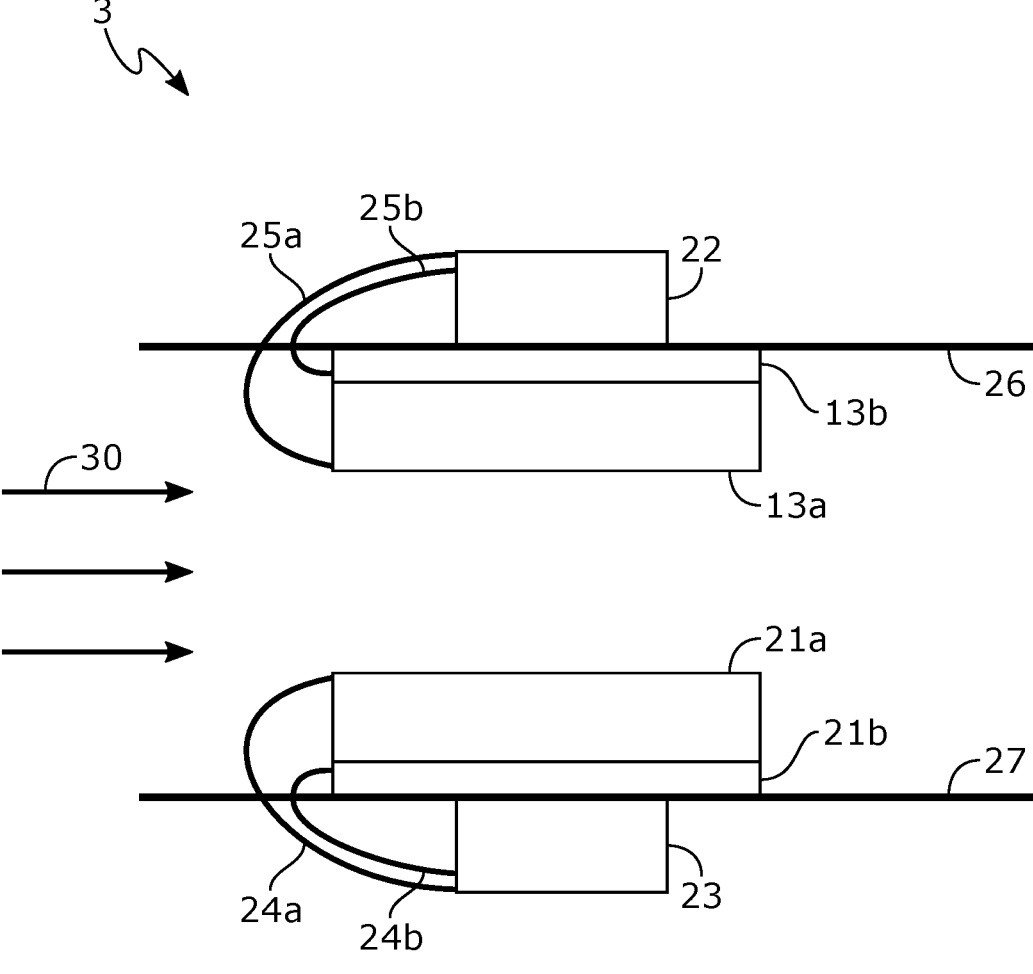
FIG. 2 depicts an embodiment of a plasma generator from a side profile.

Referring now to FIG. 2, the plasma generator (3) is depicted in a side profile view, with air (30) being depicted as flowing from left to right. In order to generate sufficient amounts of plasma, the plasma generator (3) includes stacks of electrodes, namely, upper electrodes (13) and lower electrodes (21). In FIG. 2, the upper electrodes (13a and 13b) are stacked, with each having an attached wiring harness (25a and 25b) and connected to a power source (22). The entire upper set of electrodes is attached to an upper wall (26), which allows for air to pass between electrodes within the chamber. The lower or bottom portion is a mirror image, with a lower electrode set (21a and 21b), each having a wiring harness (24a and 24b), and connected to a power source (23), and all of this is connected to a lower wall (27). Here, four electrodes are positioned stacked side by side to one another, with air and/or microdroplets passing between the electrodes.

The electrodes can be sized and the voltage appropriately modified based on the necessary output of plasma. For example, voltage of between 15 kV and 30 kV at 25-40 kHz, with a 100% duty cycle can generate nonthermal plasma. In one embodiment, the pulses have a k-kV/ns-1 rise time and 2-μs pulse duration and are single polarity positive. Appropriate voltage and amplitude are paired with airflow rate and the size and number of electrodes to yield appropriate quantities of plasma to generate reactive species within a given time period. Those of ordinary skill in the art will recognize that the voltage and frequency, as well as the pulse time and duration can be modified to meet the needs of the particular use.

Accordingly, stacking electrodes (on the top and bottom) as depicted in FIG. 2 allows for one efficient way to increase the surface area of the electrodes with the passing air. However, a second or third set, or more, as necessary, can be positioned adjacent to the first set, to be in line with the flow of air, or alternatively, positioned parallel within a wider plasma generator. For example, this is depicted in FIG. 1, with a first set (13 and 21) and a second set (42 and 43), positioned adjacent, but behind the first set (relative to the flow of air past the electrodes). The total number of sets of electrodes will depend on the volume of air passing over the electrodes and the total amount of plasma necessary to fill the space in any container, in order to reach between 0.1 ppm and 1,000 ppm of plasma-generated reactive species, inclusive of all numbers and ranges therein. For example, a measurement of plasma concentration may be a measure of the concentration of ozone. In a preferred embodiment, the concentration is >5 ppm of ozone as dissolved into microdroplets of fluid, which stabilize the RONS species. Certain embodiments have concentrations of >6, >7, >8, >9, and greater than 10 ppm ozone concentration. The size of the generators and the total flow of air will depend on the time necessary to fill the space to reach the necessary killing concentration.

Figure 3A:
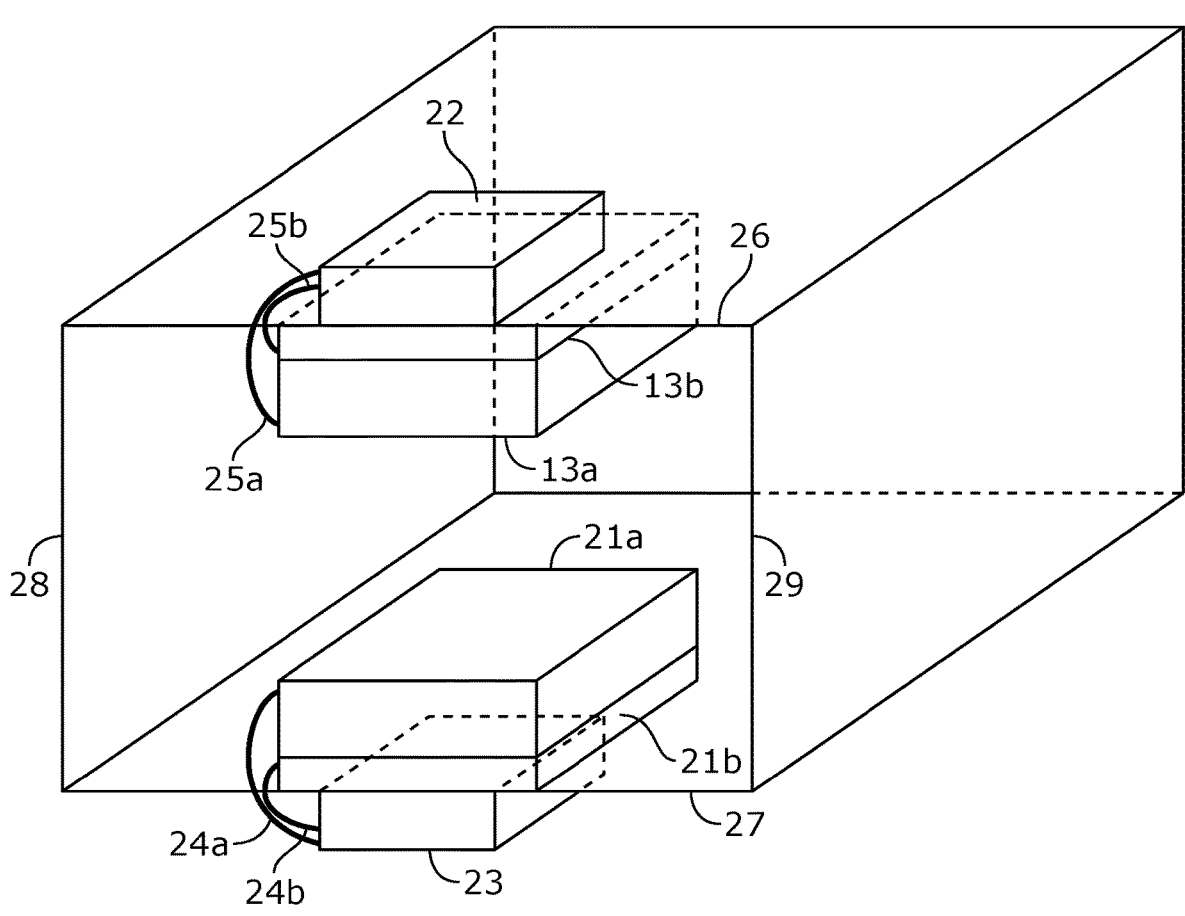
FIGS. 3A and 3B depict a front profile of a plasma generator in FIG. 3A and an exploded view of a plasma generator in FIG. 3B.
Figure 3B:
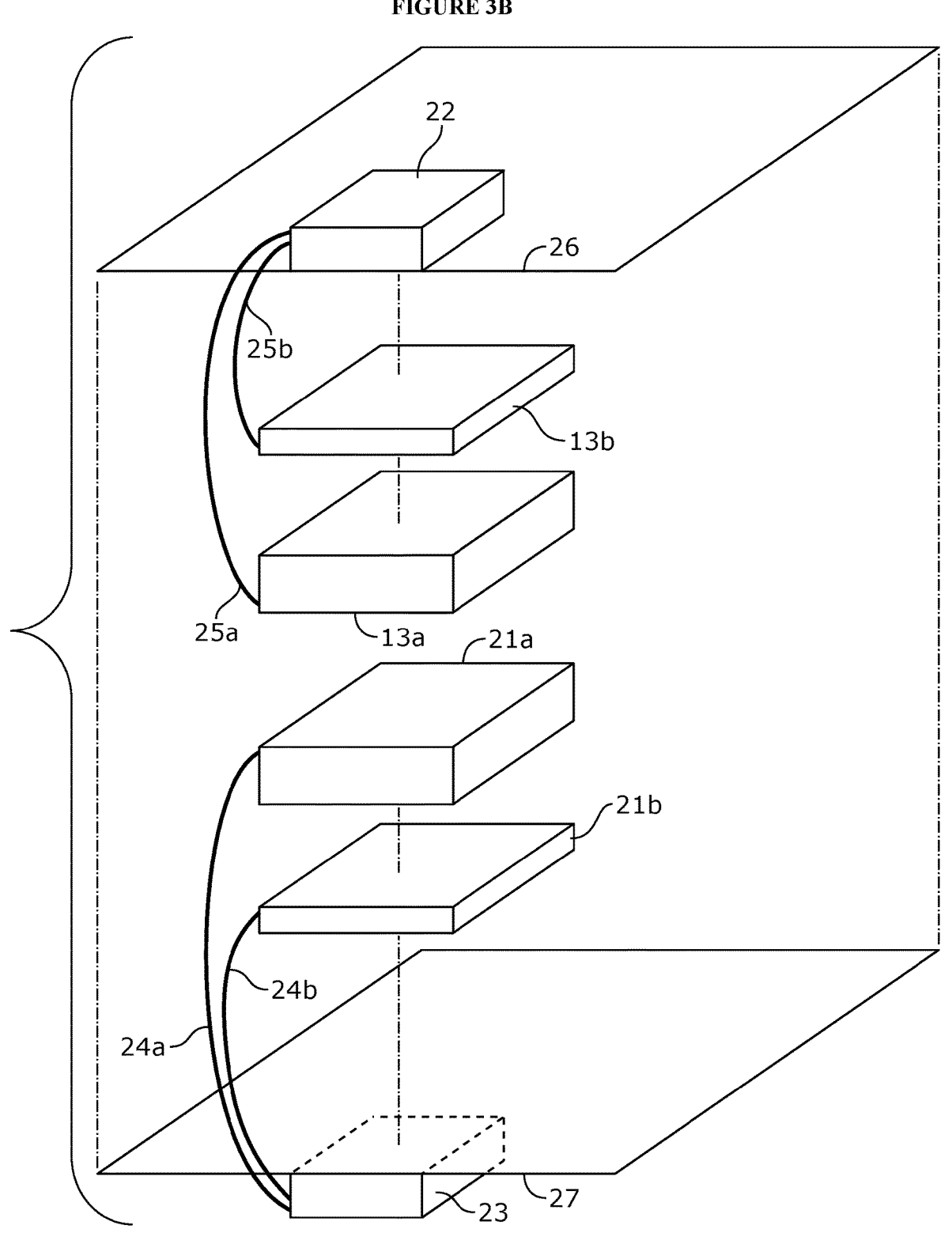

FIG. 3A depicts the plasma generator from a front position, depicting the chamber having an upper wall (26), a lower wall (27), and the sides (28 and 29), where airflows through the chamber and passes over the stacked electrodes as previously detailed in FIG. 2. FIG. 3B depicts an exploded view of the electrodes being stacked, attached to an upper wall (26), and a lower wall (27), with the electrical components, namely the electrodes, the power source and the wiring harnesses attached for each of the top set, electrodes (13a and 13b), power source (22), and wiring harness (25a and 25b), and the lower set, with electrodes (21a and 21b), with power source (23), and wiring harnesses (24a and 24b).

Figure 4:
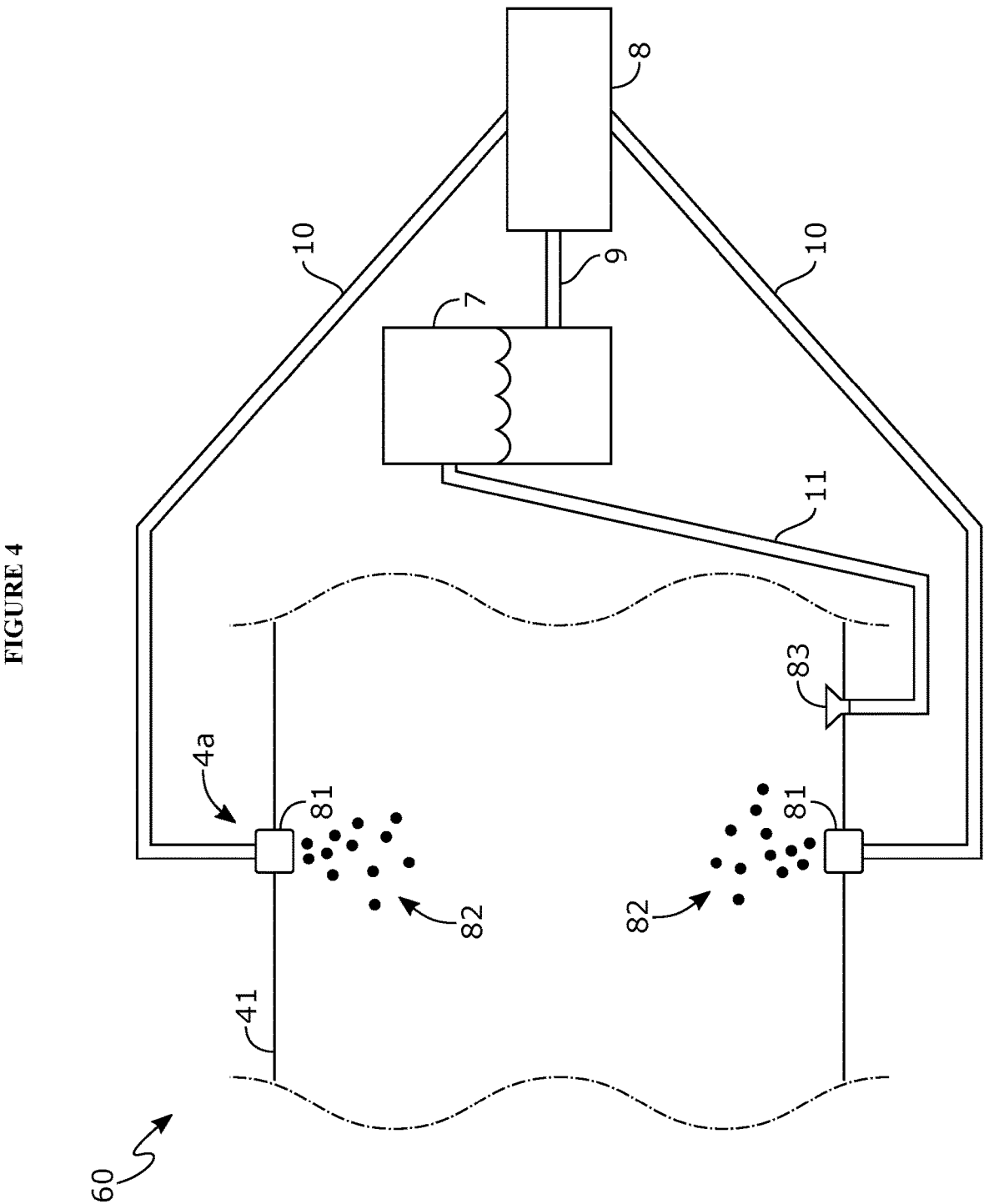
FIG. 4 depicts an embodiment of a fluidized microdroplet generator.

FIG. 4 details the fluidized microdroplet generator (60). The fluidized microdroplet generator (60) comprises several components from FIGS. 1A and 1B and is responsible for introducing microdroplets (82) of fluid, which are expelled from the nozzles (81), which are placed into the intake ports (4a, 4b, and 4c). As previously detailed, the pump (8) connected to tubing (10) expels fluids through the nozzles (81) at ports (4a, 4b, and 4c) into the fluid atomizer cavity (41). Notably, the fluid atomizer cavity (41) is a continuous space between the nozzles (81) on one end and the blade (14) of the centrifugal mixing chamber. It serves as a point at which microdroplets enter the rotational space. These microdroplets can then either be combined with the RONS as in FIG. 1A or passed through the plasma generator (3) as in FIG. 1B. If and when larger droplets are coalesced or condensed into a liquid, the fluid reaches drain (83) and can then exit through the drain line (11). The drain line can revert back to the reservoir (7), and then the pump (8) can draw fluids from the reservoir via the tubing (9), or to a drain.

The purpose of the fluidized microdroplet generator (60) is to introduce droplets of fluid into the fluid atomizer cavity (41) where they can contact the RONS species generated by the plasma generator. Notably, as detailed in FIG. 9, the presence of plasma creates sub-micron droplets itself, as the plasma causes the microdroplets to explode. Furthermore, generating micron sized droplets increases the efficiency of the system, because smaller droplets coat perishable items more efficiently than larger droplets.

Figure 5A:
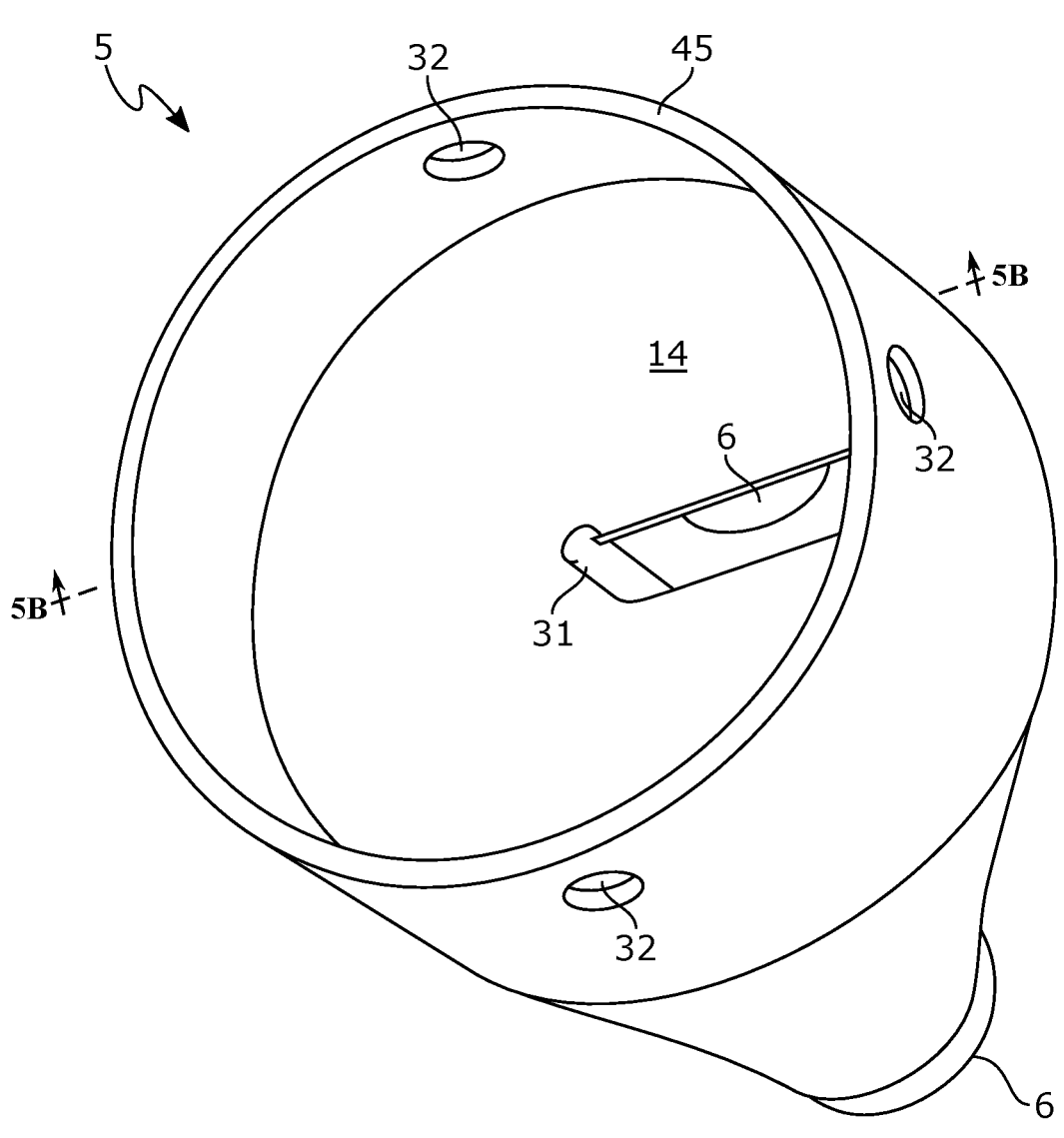
FIGS. 5A and 5B depicts a centrifugal mixing chamber, with FIG. 5A depicting a top perspective view and FIG. 5B depicting a cross-sectional view, so as to better show the blade assembly.
Figure 5B:
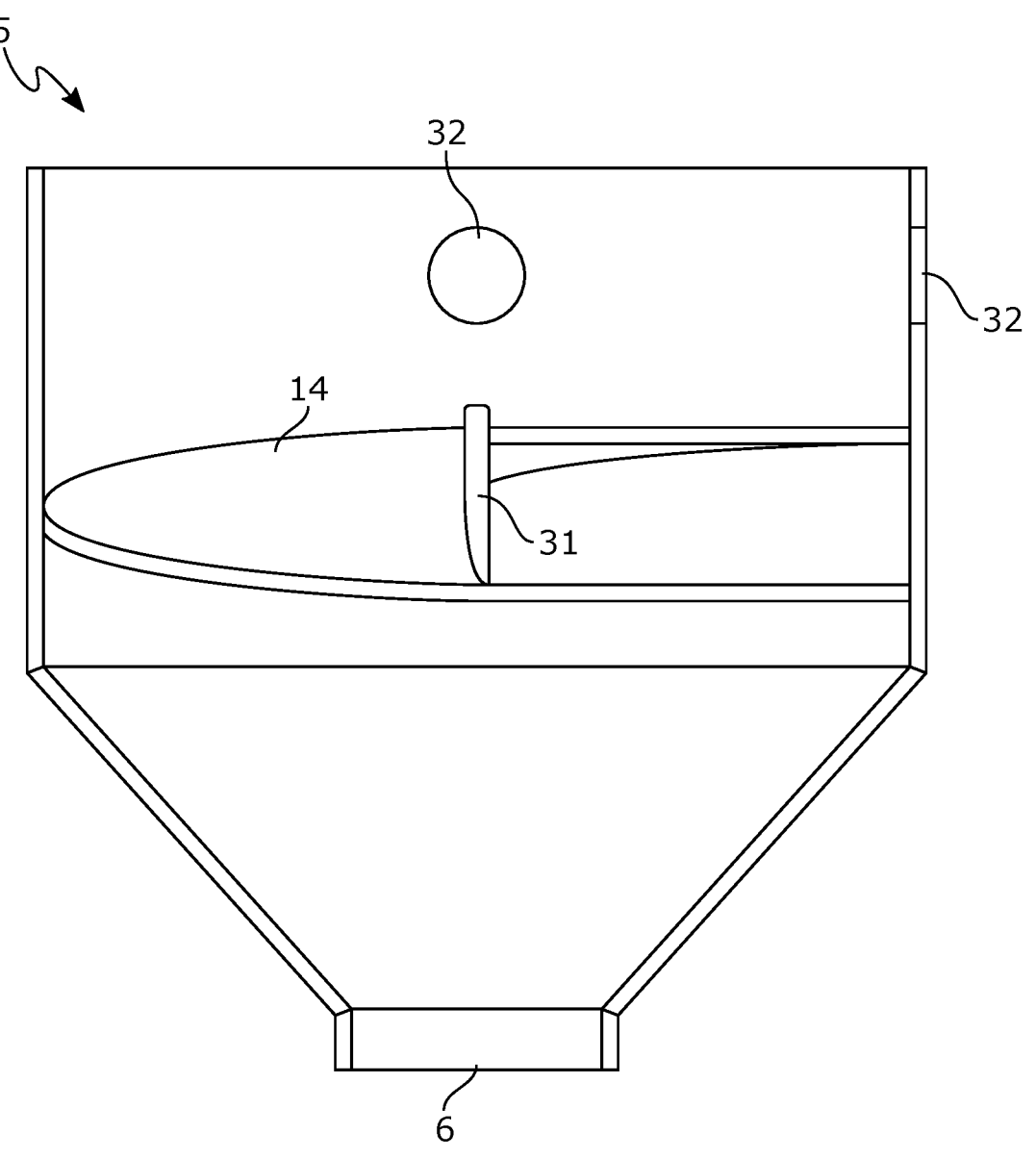
Figure 6:
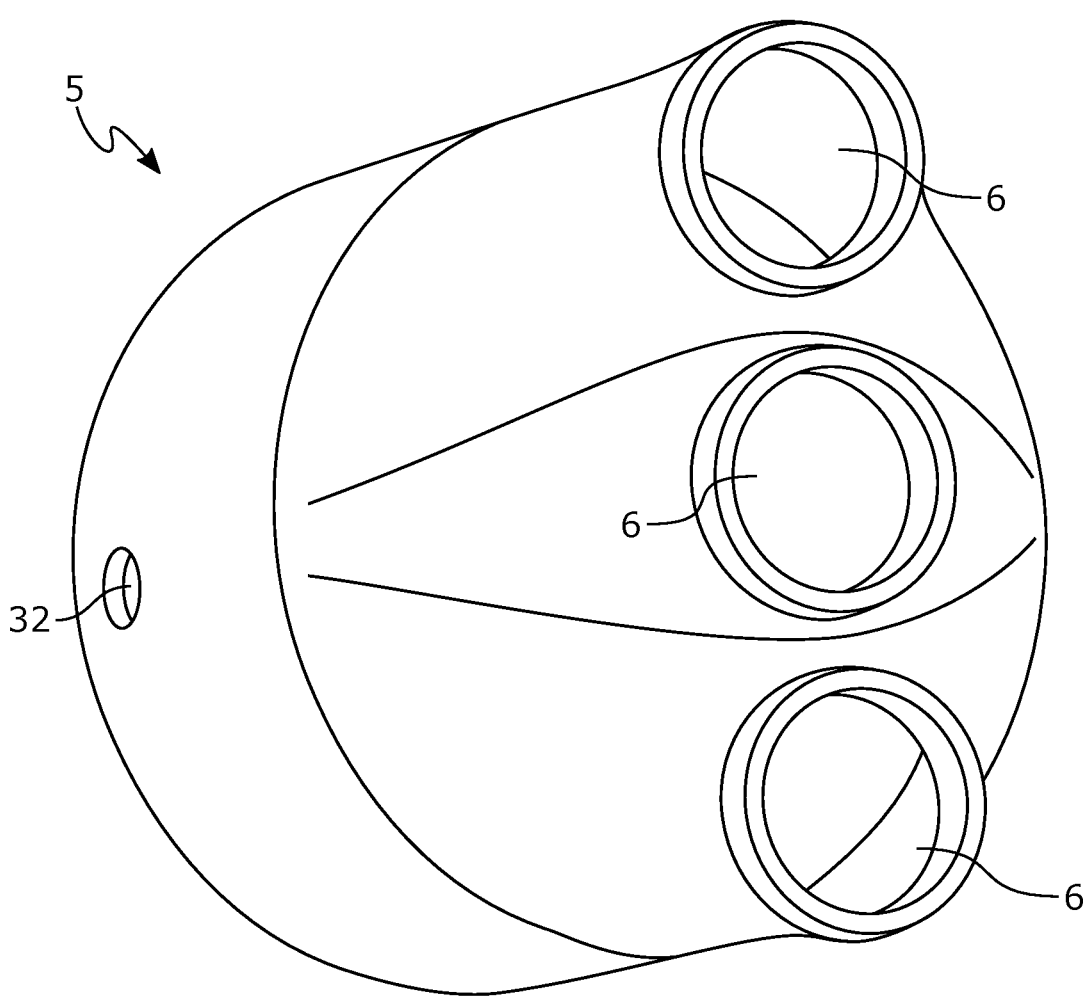
FIG. 6 depicts a bottom perspective view of a centrifugal mixing chamber.

FIGS. 5A, 5B, and 6 detail the centrifugal mixing chamber (5) with specificity. FIG. 5A shows a top perspective view, showing the blade (14), which functions like an auger blade around a central post (31). The side wall (45) is circular in shape, allowing the charged microdroplets and air to rotate easily around the blade (14) from one end to the other. In the side wall (45) is at least one opening, but depicted here with three openings (32), wherein atomization nozzles (81) are located to release the charged microdroplets and air out of the nozzles (6). There is at least one exit nozzle or port, but depicted here with three exit nozzles (6). The section between the openings (32) and the blade (14) is the fluid atomization cavity (41). These aspects are more particular shown in the cross-sectional view of FIG. 5B, which shows the angle of the blade (14), allowing air and microdroplets to rotate around the blade and move from one end of the centrifugal mixing chamber (5) to the other.

The centrifugal mixing chamber (5) forces rotation of air and the microdroplets, thus ensuring additional time for the RONS to contact the microdroplets and dissolve therein. Furthermore, the rotational design means that heavier and larger droplets will not easily pass through the rotation of the blade (14) and thus will coalesce or condense on the surfaces of the blade and walls, and then be collected through the drain line (11). This ensures that where the microdroplets are passing through the plasma generator, the size of the microdroplets will be controlled by this rotational sorting. Or, if the microdroplets are being combined with RONS from the plasma generator, the microdroplets that are expelled are smaller in size distribution.

FIG. 6 shows a perspective view from the exit nozzle (6) end and depicting one of the side wall openings (32). Depending on the orientation, the exit nozzle (6) can be one or more openings, and open to expel microdroplets to their ultimate destination, or through the plasma generator (3) to charge the microdroplets.

In certain embodiments, the charged microdroplets can then be utilized to coat perishable items. For example, when the charged microdroplets are expelled from the device, they can be blown into a chamber (70), wherein the charged microdroplets (82) then cover the contents of the container. For example, a container may be a storage container holding any perishable item. By providing a sufficient density of charged microdroplets, the microdroplets are able to quickly and evenly cover the materials inside of the storage container with the charged microdroplets. In turn, the charged microdroplets are thus able to disinfect, sanitize, and/or sterilize the surfaces they are contacting.

Therefore, the device can be advantageously attached to a container or storage device, wherein the fan (2) is engaged to blow air across the electrodes. The air can then either pass over the electrodes and be combined with microdroplets, or the microdroplets can be introduced before the electrodes. In either iteration, the microdroplets are charged with reactive species by dissolving the RONS into the microdroplets.

Figure 7:
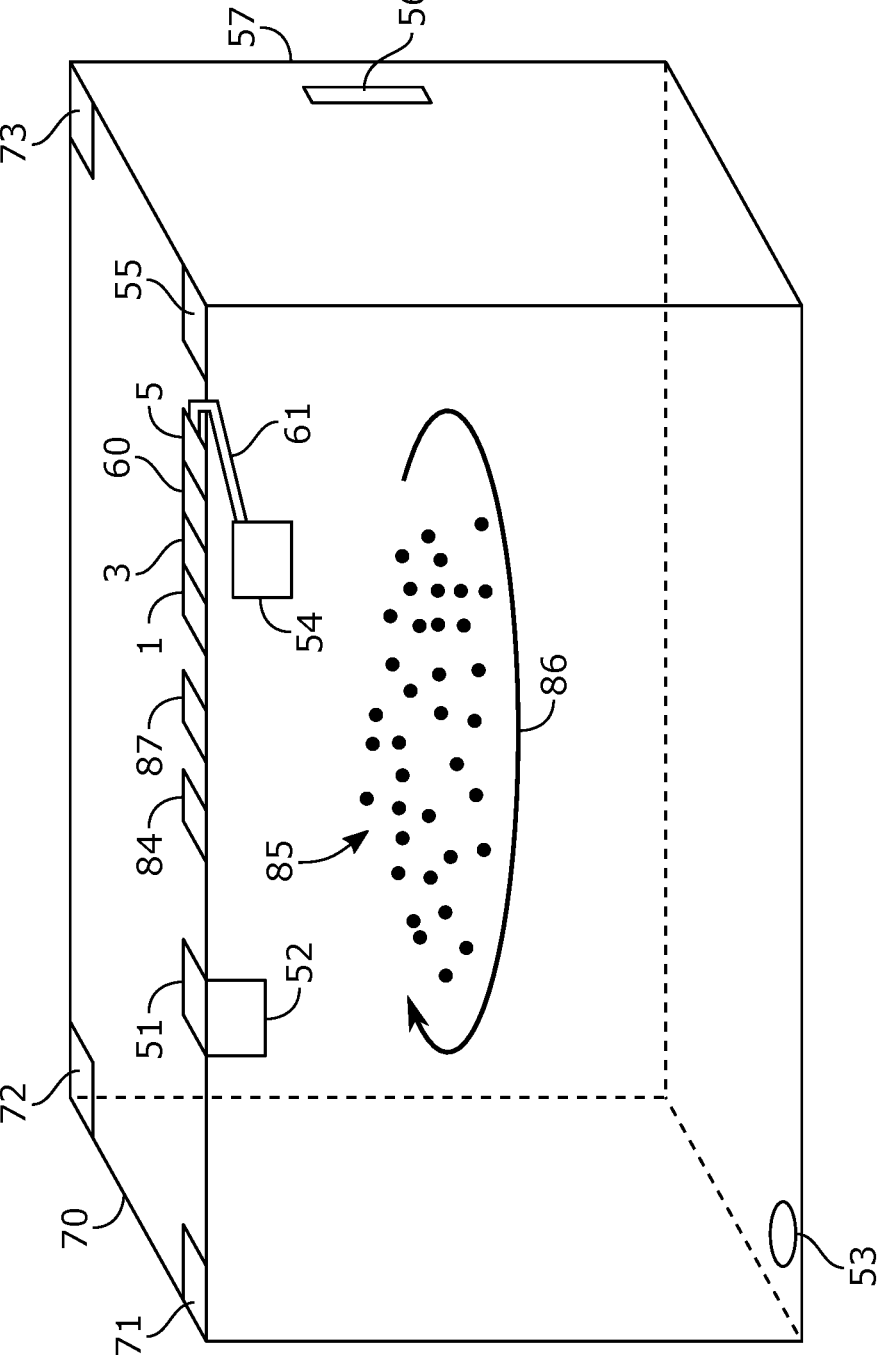
FIG. 7 depicts an embodiment of a plasma generating device attached to a vacuum chamber.

FIG. 7 details an embodiment, wherein the device is attached to a chamber (70). The chamber (70), for example, a vacuum container, which can be of any size and shape, but preferably one of standard sized shipping containers, comprises a vacuum pump (51) and a vacuum opening (52) which can create the vacuum and evacuate the chamber (70). A drain (53) is located at the bottom of the chamber (70), which can drain fluids, or also serve as a valve to open the chamber (70) to ambient pressure. A door (57) on hinges (55) is attached to one end, with a locking mechanism (56), to allow the chamber to be sealed and to reach lower or higher pressures than ambient pressure. Mounted on the chamber (70) is a plasma generating device for generating plasma dissolved in microdroplets of fluid.

In FIG. 7, the plasma generating device is located on the top of the chamber (though it can be located anywhere on the device), and the plasma generating device is connected fluidly with an opening (54) into the chamber to allow for transfer of gasses and fluids through the plasma generating device and into the chamber (70). The chamber (70) is closed for a predetermined amount of time, i.e., at least as long as necessary to generate charged microdroplets and coat the materials therein for at least 30 seconds. Typically, the chamber (70) is thus closed for at least thirty seconds, with no upper time limit, e.g., until the doors are opened to move materials therein, or for air exchange for cooling or other purposes. Alternatively, the closed duration can be a set amount of time, i.e., between 30 seconds and 24 hours, with all values in between.

The plasma generating device comprises an air filter (1), a plasma generator (3), a fluidized microdroplet generator (60), and a mixing chamber (5). The air filter (1) is as previously detailed in FIGS. 1A and 1B, as is the plasma generator (3) and the mixing chamber (5). The fluidized microdroplet generator (60), as detailed in FIG. 4 comprises at least the reservoir (7), a pump (8), a fluid atomizer cavity (41), tubing (10), and atomizing nozzles (81), which atomize microdroplets (82) of fluid. Each of the air filter (1), plasma generator (3), fluidized microdroplet generator (60), and mixing chamber (5) are in fluid communication with one another, with the plasma generator (3) and the fluidized microdroplet generator (60) being before or after one another. A power source (87) is connected to the components in order to provide the necessary power to operate the devices. An operating system (84) is preferably a computer-controlled system, which is utilized to control the various electrical components, valves, fans, and the like. Each of the components can be connected via wire or wireless connection, as understood by one of ordinary skill in the art.

The plasma generating device functions by passing air through the air filter (1), which connects to the plasma generator (3), which connects to the fluidized microdroplet generator (60), and to the mixing chamber (5), and finally to a connection apparatus (61) which connects to the opening (54) and generates a concentration of reactive species dissolved into microdroplets of fluid. The connection apparatus (61) can simply be a valve or gasket or can be a series of tubes or pipes to allow for efficient connection between the mixing chamber (5), specifically to the nozzles (6) at the distal end of the mixing chamber (5), and to the chamber (70) itself. The position of the fluidized microdroplet generator (60) and the plasma generator (3) can be reversed, so that the fluidized microdroplet generator (60) is positioned before the plasma generator (3).

In this embodiment, the device can function without the use of a fan (2) or other air generator as it utilizes negative pressure created by the vacuum to draw air through the system. Accordingly, when a vacuum is pulled within the chamber (70) and then the vacuum is released, a volume of air is rapidly pulled into the chamber (70) to equalize the pressure. By using a specific opening or valve, we know that air will rush from outside of the chamber (70) into the chamber through this opening. Here, the vacuum is released at the opening (54), which is in fluid connection with the plasma generating device and thus pulls air through the air filter (1), through the combination of the plasma generator (3), microdroplet generator (60), and mixing chamber (5) and then through the connection apparatus (61), which expels the microdroplets into the chamber (70), thereby filling the chamber (70) with reactive species which are dissolved into the microdroplets (85). These microdroplets (85) will then be circulated (86) throughout the chamber (70) and cover the contents of the chamber with the reactive species within the microdroplets (85). Notably, the orientation of the plasma generator (3) and the microdroplet generator (60) can be reversed, so that the microdroplets are formed before entering the plasma generator (3).

The generating of a vacuum and then release of that vacuum through one or more ports, which are attached to the plasma generating device ensures a consistent draw of air for a known amount of time, to generate a reproducible amount of RONS to be dissolved into the microdroplets. The RONS are inherently unstable, and while they are strong oxidizers, they are stabilized by being dissolved into fluid. However, the fluid retains the oxidative properties and shows dramatic reduction in bacterial loads in just a few seconds.

In order to efficiently cover any contents within a chamber (70), the chamber (70) may further comprise one or more fans (71, 72, and 73), which can aid in the mixing and circulation (86) of air within the chamber (70). This simply provides additional airflow to ensure that the reactive microdroplets (85) are able to completely cover and saturate the contents of the chamber (70). Because of the airflow and the small size of the microdroplets, the microdroplets are able to enter packaging (think of the moisture found in packed produce), as well as to coat both the top and bottom and side surfaces of the produce as the microdroplets are circulated.

In certain embodiments, a fan (2) can be added in between the air filter (1) and the plasma generator (3), as is depicted in FIGS. 1A and 1B, to additionally aid in blowing air, in addition to the air being pulled by the vacuum, or, as needed, where no vacuum is utilized in a chamber (70). Thus, in a chamber without vacuum, a simple fan (2) can provide for the air movement necessary to create the charged microparticles and to circulate them through the chamber.

In order to properly sanitize, disinfect, and/or sterilize the contents of a chamber (70), a dwell time of at least thirty seconds on the surface of materials within the chamber (70) is preferred, as compared to 10 seconds and 20 seconds of contact. However, additional time may be utilized without damage to the perishable items in most cases. Accordingly, after the chamber (70) reaches saturation, for example between 1 minute and 2 minutes after the start of introduction of the microdroplets (85) into the chamber (70), a dwell period is used before the chamber (70) should be further evacuated. In many cases, the microdroplets (85) will remain on the perishable items without damage to the surface of the skin or to other components. Thus, the microdroplets (85) can be washed off with a rinse, can be simply maintained on the surface, or a further component, such as UV lights or something similar can be utilized to destroy reactive species or provide another layer of sterilization. These components can destroy the reactive species, thus ensuring that release of the chamber does not release RONS species into the atmosphere. To evacuate the chamber, the chamber can simply be opened, allowing any ozone or other RONS to be dissipated into the environment. Thus, a predetermined amount of time for disinfection is typically between 30 seconds and several hours, wherein the microdroplets can thereafter be released to ambient air for dissipating.

In a preferred embodiment, when utilizing a large container such as a 57 m$^3$ transport container, the preferred flow rate through the device is approximately 1500 cfm, which offers ideal mixing, but a range of 100 cfm to 10,000 cfm is suitable for various embodiments. In the particular example, using simple math: 1,500 cfm yields 42.475 m$^3$/min and thus to fill the 75 m$^3$ chamber (70) it takes approximately 1.34 minutes to fill the volume of the chamber (70). Where 10 grams/hour of ozone is generated, it yields 0.1667 grams of ozone per minute, or 0.2233 g per each plasma generator. 1 gram/m$^3$ is equivalent to 467 ppm of ozone (which is generated by the plasma generator) in the air. Thus, assuming 1.34 minutes and 1,500 cfm, each plasma generator as described herein yields approximately 1.83 ppm of ozone as dissolved into the microdroplets in the 57 m$^3$ container. Thus, to reach a concentration of >5 ppm, a total of between three and four plasma generators are needed, based on the actual time in which the plasma generators are charged.

Where the volume of the chamber (70) is smaller or larger, or the total time of the airflow transfer is shorter or longer, the appropriate modification of the device can be made to include fewer or more plasma generators to reach the appropriate concentration of ozone. The device can be easily modified to have larger plasma generators or include more plasma generators either parallel or in series with those depicted herein. Those of ordinary skill in the art will recognize the ability to calculate the volume of a container and the time to fill the container with a given volume of air and therefore be able to calculate the required ozone generation to create the suitable ppm necessary.

Notably, when loaded with RONS, the charged microdroplets are acidic, around pH of 2.0. The fluid used in the reservoir (7) is preferably non-DI or RO-DI water, as tap water or well water, natural flowing water, or otherwise reconstituted water containing metallic ions. Thus, the iron and/or other multivalent metals, as required for Fenton's reaction will be present in the fluid to allow for Fenton's mechanism to proceed. Furthermore, additional metallic ions will be present in tap or well water and which also stabilize RONS species.

The fluid in reservoir (7) may be water, or it may further comprise additional excipients such as: acids, bases, buffer solutions (comprising a conjugate acid and base), peroxide solutions, bleach, peracetic acid, etc. Preferably, the concentration is between 50% and 100% water and between 0% and 50% of an additional excipient, for example a 10% peroxide and 90% water solution. Notably, the inclusion of a 10% solution was determined to be exponentially better at reduction in pathogens as compared to a 100% water or 100% peroxide solution. This same evidence was also found with the addition of other excipients. However, such additives may be disadvantageous in certain applications.

Those of skill in the art will recognize that fluid can be atomized into very fine microdroplets via the atomizer or nebulizer component, which generate tremendous surface area. The microdroplets mix with the air that is charged from the electrodes. The electrodes generate nonthermal plasma with a 20 kHz 3,000 V setting. Because air contains both oxygen and nitrogen compounds, when these air molecules pass the dielectric barrier discharge (electrodes) a variety of reactive species are generated. However, these reactive species are typically unstable. Accordingly, there is a need to stabilize the reactive species so that they can then attack pathogenic materials. Typically, we are looking for strong oxidizing species and protecting these with fluid. When combined with the atomized microdroplets (82) from the nozzle (81), species such as ozone (O$_3$), hydroxyl radical (OH), hydrogen peroxide (H$_2$O$_2$), singlet oxygen (O$_2$*), peroxynitrite radical (ONOO*), are generated, conserved, and protected by being dissolved into fluid droplets. It is these radicals, most specifically the ozone, peroxides, and peroxynitrite which are the key effectors in reducing bacterial and viral loads.

A key feature of the atomized microdroplets is their size. While a typical atomizer may be effective in generating droplets of fluid, these are typically only as small as 5-100 microns. However, by reducing the size of the microdroplets to below ten microns, the total surface area of the microdroplets can be dramatically increased. This is critically important as the greater surface area increases the rate of uptake of the radical species into the microdroplets. Furthermore, once generated, the greater surface area and sheer number of microdroplets ensures that the RONS microdroplets are in sufficient quantities and density to saturate the surface of the materials being disinfected.

The microdroplets are expelled from the exit nozzle (6) and into the container where the size of the microdroplets and the concentration are important for ensuring saturation of the materials. Because of the small size, the microdroplets are effective in fully and evenly coating surfaces of materials within the container. Thus, where *E. coli* or other microorganisms are present on the surface of the materials within the container, we can destroy these materials with the microdroplets, even without the Fenton reaction and without excipients. However, in the presence of iron, there will be even stronger oxidization and thus more effective killing of the various pathogens.

Figure 8:
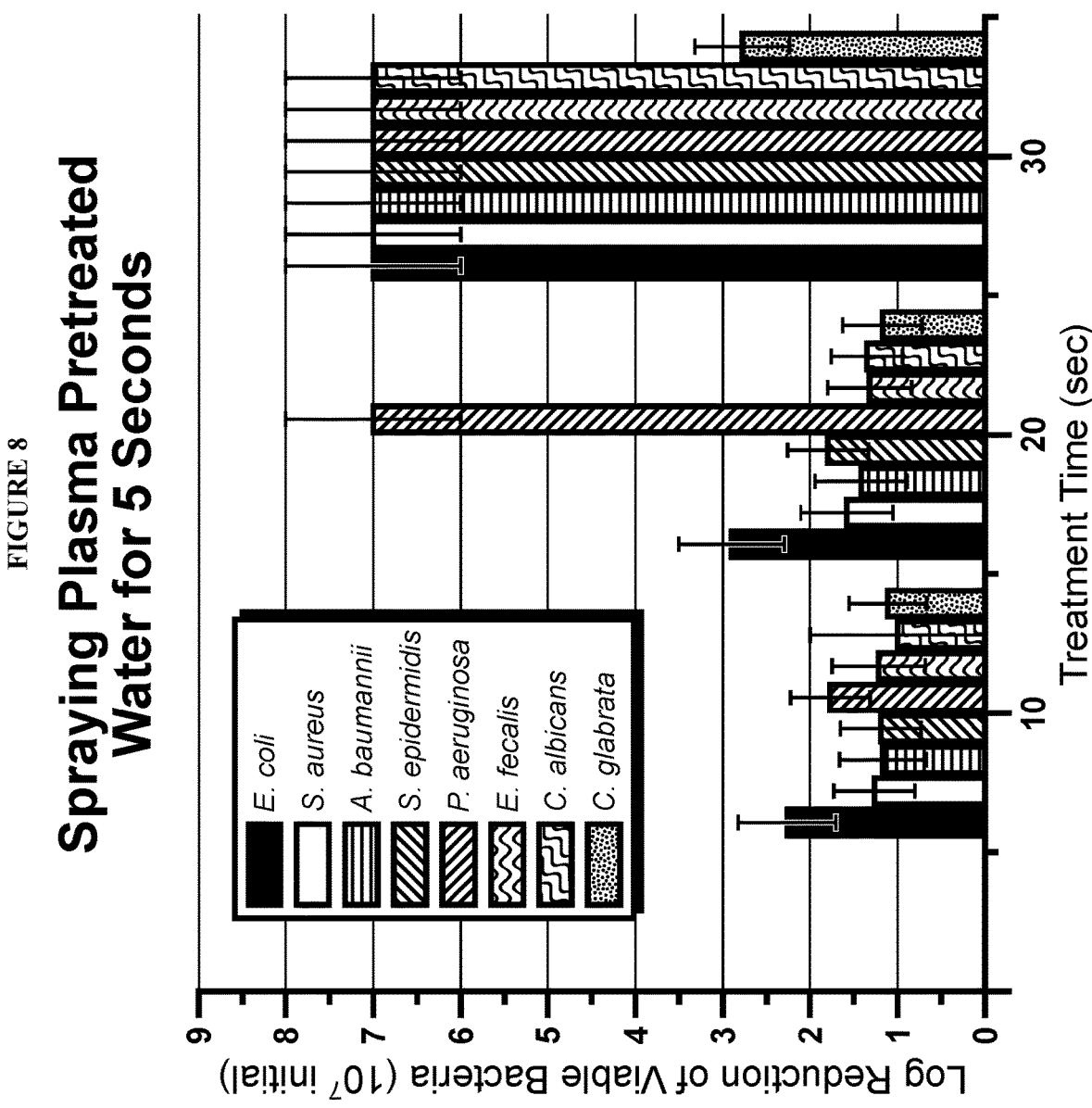
FIG. 8 depicts a graphical chart identifying that by spraying plasma pretreated water over certain time periods has a different log reduction and can increase to a greater than 5-log reduction of bacteria upon an increase in dwell time from 20 seconds to 30 seconds.

Accordingly, as depicted in FIG. 8, the charged microdroplets can be sprayed over perishable items for a given period of time to reduce loads of pathogens. Notably, increasing the time of treatment from 10 seconds to 30 seconds dramatically increases the log reduction of the pathogens. The method of filling a chamber with the microdroplets is highly effective in mixing, saturating, and evenly distributing the microdroplets over the surface of perishable items within the container for more than 30 seconds to ensure that necessary log reduction in pathogenic loads as necessary for sterilization protocols.

Figure 9A:
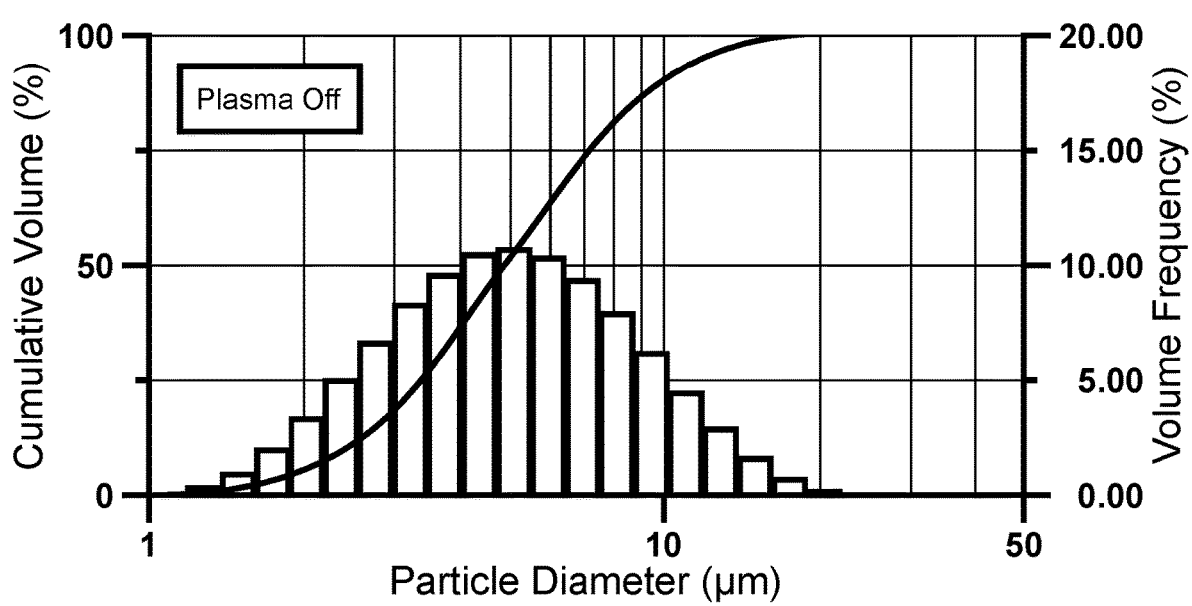
FIGS. 9A, 9B, and 9C depict that plasma creates submicron droplets of fluid.
Figure 9B:
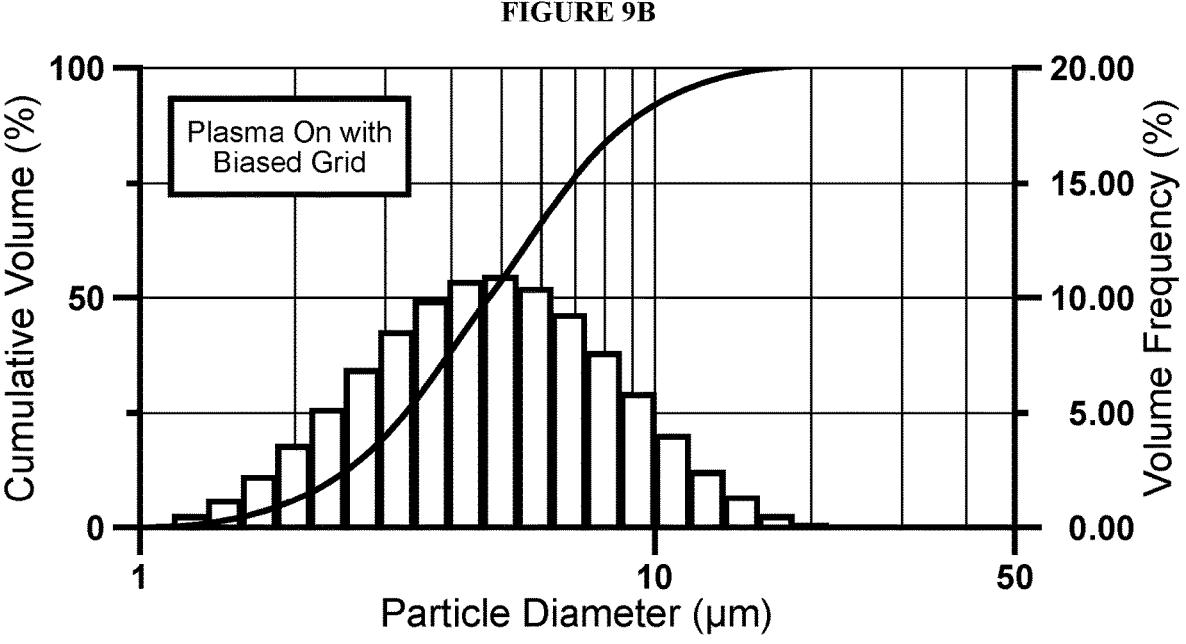
Figure 9C:
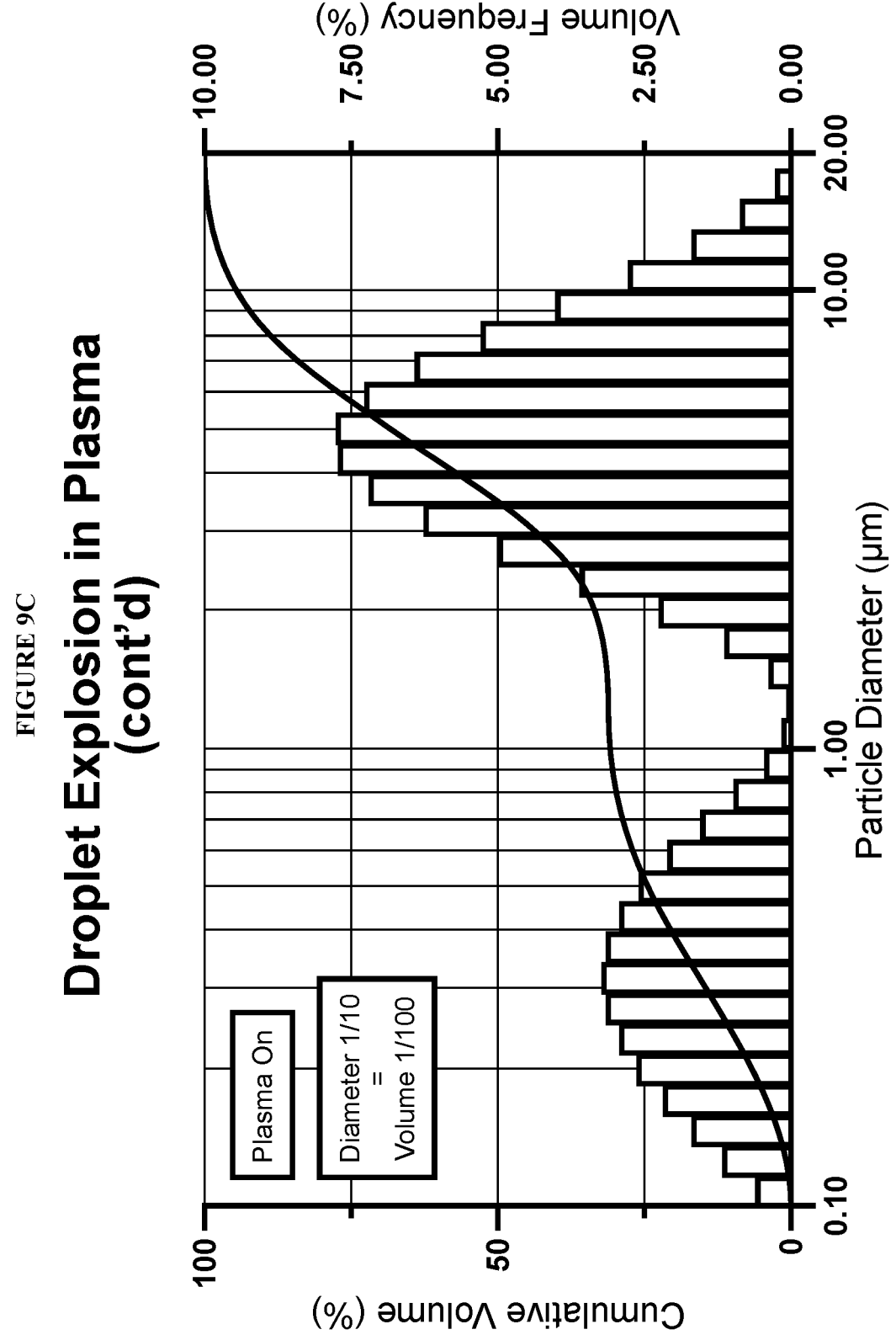

Indeed, the even coating of the microdroplets is effectively created by the small size or the microdroplets. FIG. 9 depicts that plasma in itself creates small diameter microdroplets of fluids, and thus creates a higher efficiency of treatment to the pathogenic loads. The introduction of plasma creates coulombic explosion of droplets to reduce the radius of the droplets. The microdroplets of the present disclosure are created and maintained along a bell curve for their size. By using plasma, much smaller droplets of the fluid are created than are initially created by the nozzles alone.

In order to disinfect and reduce the pathogenic load on surfaces of perishable items, a certain concentration of reactive species is necessary. Thus, the volume of the container being disinfected and the surface area of the materials within that container are important to quantify. For example, a vacuum chilling container which rides on a tractor trailer and hauled by a truck or can be placed on rail or cargo ship. This type of container would be utilized to rapidly cool produce or other perishable items to reduce the temperature to between 33° F. and 40° F. Typically, the temperature is reduced to just above freezing, but not to or below freezing, as the action of freezing can damage the produce once it is thawed. However, by reducing temperatures, dramatic increases in shelf life are achieved to produce as is known to those of ordinary skill in the art.

The vacuum chamber utilizes a vacuum to evacuate the air from within the chamber. Once the pressure is reduced within the chamber, opening of a valve will quickly return pressure to the chamber by mixing of air through the opening into the chamber. We can utilize this air transfer to our advantage to pull air through the system.

In a preferred embodiment, the device is attached to a pressurized chamber, wherein release of the pressure from within the chamber is used by the plasma generating device. For example, a method of sanitizing perishable items comprises: generating a vacuum, and chilling the materials within the vacuum chamber; activating the plasma device and opening a valve connected to the plasma generating device; the release of the vacuum pulls air through the air filter of the plasma generating device, and then the air admixes with the expressed microdroplets, which and across the electrodes to generate RONS; wherein fluid is expressed into the atomizer cavity and then circulated around the centrifugal mixing chamber to increase both the dwell time of the RONS with the expressed fluids, to yield charged microdroplets and to reduce the average size of the microdroplets; and expelling the charged microdroplets, into the container. This leaves the vacuum chamber at ambient pressure. If chilling is needed in the chamber, the chamber can be chilled or a vacuum pulled again, after sufficient time for the charged microdroplets to sit on the perishable items within the chamber.

This method quickly and safely provides for sanitization, disinfection, and sterilization of perishable items with minimal fluid or fluid waste and without the need for or use of toxic chemicals, as the reactive species will degrade rapidly into nonreactive species which are innocuous after a short amount of time. However, these reactive species remain active to oxidize pathogens for at least 30 seconds, and most likely will remain active for several minutes at a minimum. These charged microdroplets can then be evacuated through the ambient air.

Applicant recognizes that several of the components of the invention can be modified without deviating from the scope of the invention and yield the objective of sanitizing, disinfecting, and sterilizing the perishable items, and that those of ordinary skill in the art will recognize that simple modification may be necessary to retrofit devices onto different vacuum chambers or to meet requirements for specific produce or perishable items.

What is claimed is:

1. A device for creating charged microdroplets comprising: a centrifugal mixing chamber for receiving atomized microdroplets, a plasma generator comprising at least one electrode positioned within an open-ended chamber; wherein said centrifugal mixing chamber comprises a central post and a blade structure defining a centrifugal path around the central post to orient a flow of air and microdroplets from one end of the centrifugal mixing chamber to a second end.

2. The device of claim 1 wherein the plasma generator is positioned before the centrifugal mixing chamber.

3. The device of claim 2 wherein said open-ended chamber having a first end and a second end, with the first end and the second end open to allow passage of air through the open-ended chamber; an air filter positioned at the first end; and an atomizing cavity having a first cavity end in fluid contact with the second end, a second cavity end, and a side wall, said side wall comprising at least one aperture thereto, and at least one nozzle affixed into said aperture; wherein the centrifugal mixing chamber is contiguous with the second cavity end, said centrifugal mixing chamber comprising a mixing chamber side wall and the blade, said blade oriented to allow a passage of air in a circular motion around the central post of said centrifugal mixing chamber, and an at least one exit nozzle on an opposing end of said centrifugal mixing chamber.

4. The device of claim 1 wherein the plasma generator is positioned after the centrifugal mixing chamber.

5. The device of claim 4 comprising an atomizing cavity in contact with the centrifugal mixing chamber, said atomizing cavity comprising a first cavity end and a second cavity end, and a side wall, said side wall comprising at least one aperture thereto, and at least one nozzle affixed into said aperture; wherein the centrifugal mixing chamber is contiguous with the second cavity end, said centrifugal mixing chamber comprising a mixing chamber side wall and the blade, said blade oriented to allow passage of air in a circular motion around the central post of said centrifugal mixing chamber, and an at least one exit nozzle on an opposing end of said centrifugal mixing chamber, which is in contact with the plasma generator.

6. The device of claim 1 further comprising a fan.

7. The device of claim 6 wherein the fan pulls air through an air filter.

8. The device of claim 1 further comprising a pump and a fluid vessel, said pump configured to pump fluid through at least one nozzle.

9. The device of claim 8 wherein said pump generates nebulized fluid.

10. The device of claim 8 wherein the pump is disposed of below the centrifugal mixing chamber.

11. The device of claim 10 wherein the pump is placed between 0.01 meter and 3 meters below the centrifugal mixing chamber.

12. The device of claim 8 further comprising a drain.

13. The device of claim 12 wherein the drain connects to either the fluid vessel or is disposed.

14. The device of claim 1 wherein said plasma generator comprises at least two electrodes stacked on top of one another, wherein the two electrodes are positioned to allow the flow of air above and below each of the two electrodes within the open-ended chamber.

* * * * *